(12) United States Patent
Suzuta et al.

(10) Patent No.: US 12,157,718 B2
(45) Date of Patent: Dec. 3, 2024

(54) CHEMISTRY REACTION METHOD AND CHEMISTRY REACTION DEVICE

(71) Applicant: SUMITOMO CHEMICAL COMPANY, LIMITED, Tokyo (JP)

(72) Inventors: Tetsuya Suzuta, Niihama (JP); Masato Matsuda, Niihama (JP); Takehiro Nakasuji, Ichihara (JP); Yuichi Sato, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 492 days.

(21) Appl. No.: 17/762,722

(22) PCT Filed: Sep. 17, 2020

(86) PCT No.: PCT/JP2020/035279
§ 371 (c)(1),
(2) Date: Mar. 22, 2022

(87) PCT Pub. No.: WO2021/060145
PCT Pub. Date: Apr. 1, 2021

(65) Prior Publication Data
US 2022/0363617 A1    Nov. 17, 2022

(30) Foreign Application Priority Data

Sep. 27, 2019  (JP) ................. 2019-177458

(51) Int. Cl.
*C07C 29/152*   (2006.01)
*B01J 8/02*     (2006.01)
*C07C 31/04*    (2006.01)

(52) U.S. Cl.
CPC .......... *C07C 29/152* (2013.01); *B01J 8/0257* (2013.01); *B01J 8/0285* (2013.01); *C07C 31/04* (2013.01)

(58) Field of Classification Search
CPC ...... C07C 29/152; C07C 31/04; B01J 8/0257; B01J 8/0285; B01J 2208/00123;
(Continued)

(56) References Cited

U.S. PATENT DOCUMENTS

2004/0204507 A1   10/2004   Filippi et al.
2010/0267848 A1   10/2010   Duwig et al.
(Continued)

FOREIGN PATENT DOCUMENTS

CL    200202203 A1    8/2003
CL    201000726 A    12/2010
(Continued)

OTHER PUBLICATIONS

Office Action issued in corresponding Japanese Patent Application No. 2021-548859 dated Mar. 12, 2024 (4 pages).
(Continued)

*Primary Examiner* — Jafar F Parsa
(74) *Attorney, Agent, or Firm* — Foley & Lardner LLP

(57) ABSTRACT

A source material gas (31) is supplied to a catalyst (30), a first heating medium (21) is caused to flow through a first heat exchange section (22) so that a temperature of a surface of the first heat exchange section (22) on a catalyst side is maintained higher than a dew point of a reacted gas (32), a second heating medium (51) is caused to flow through a second heat exchange section (52) so that a temperature of a surface of the second heat exchange section (52) on a space (4) side is maintained not higher than the dew point of the reacted gas (32), and a liquid obtained by condensation in the space (4) is allowed to fall down so as to be separated from the source material gas.

9 Claims, 7 Drawing Sheets

(58) Field of Classification Search
CPC .................. B01J 2208/00212; B01J 8/0242; B01J 8/067; B01J 19/2475; B01J 8/02
See application file for complete search history.

(56) References Cited

U.S. PATENT DOCUMENTS

| | | |
|---|---|---|
| 2010/0305222 A1 | 12/2010 | Thorhauge |
| 2010/0312021 A1 | 12/2010 | Thorhauge |
| 2012/0269697 A1 | 10/2012 | Thorhauge |
| 2012/0308442 A1 | 12/2012 | Duwig et al. |
| 2013/0203872 A1 | 8/2013 | Laurenzi |
| 2016/0200572 A1 | 7/2016 | Xie |
| 2023/0311092 A1 | 10/2023 | Nakasuji et al. |

FOREIGN PATENT DOCUMENTS

| | | |
|---|---|---|
| CL | 201301082 A1 | 10/2013 |
| CN | 103435006 A | 12/2013 |
| CN | 115989081 A | 4/2023 |
| EP | 0 273 29 A1 | 4/1981 |
| GB | 1 405 040 A | 9/1975 |
| JP | 2000-281310 A | 10/2000 |
| JP | 2001-009265 A | 1/2001 |
| JP | 2004-149337 A | 5/2004 |
| JP | 2004-299924 A | 10/2004 |
| JP | 2005-298413 A | 10/2005 |
| JP | 2007-512458 A | 5/2007 |
| JP | 2010-013422 A | 1/2010 |
| JP | 2011-143370 A | 7/2011 |
| WO | WO-00/02655 A1 | 1/2000 |
| WO | WO-2005/052330 A1 | 6/2005 |
| WO | WO-2009/106232 A1 | 9/2009 |
| WO | WO-2010/101073 A1 | 9/2010 |

OTHER PUBLICATIONS

Partial Supplementary European Search Report issued in corresponding European Patent Application No. 20870219.1, dated Aug. 21, 2023.
Extended European Search Report, dated Oct. 16, 2023, issued in corresponding European Patent Application No. 20870219.1.
International Search Report issued in corresponding International Patent Application No. PCT/JP2020/035279 dated Nov. 24, 2020.
Written Opinion and its English Translation (International Preliminary Report on Patentability) issued in corresponding International Patent Application No. PCT/JP2020/035279 dated Nov. 24, 2020.
Office Action issued in corresponding Chinese Patent Application No. 202080066326.8 dated Mar. 25, 2024 (16 pages).
Tan Huai Shan, "Comparison of conversion technologies for large coal-to-methanol plants", Large Scale Nitrogenous Fertilizer Industry, Feb. 2018, vol. 41, No. 1, pp. 1-6.
Office Action issued in corresponding Chilean Patent Application No. 202200743 dated Jul. 28, 2023 (35 pages).
Office Action issued in corresponding Chilean Patent Application No. 202200743 dated Jan. 25, 2024 (29 pages).

CHEMISTRY REACTION METHOD AND CHEMISTRY REACTION DEVICE

CROSS-REFERENCE TO RELATED APPLICATIONS

The present application claims priority under 37 U.S.C. § 371 to International Patent Application No. PCT/JP2020/035279, filed Sep. 17, 2020, which claims priority to and the benefit of Japanese Patent Application No. 2019-177458, filed on Sep. 27, 2019. The contents of these applications are hereby incorporated by reference in their entireties.

TECHNICAL FIELD

The present invention relates to a chemical reaction device and a chemical reaction method each causing a chemical reaction for obtaining a product from a source material gas to proceed in a gaseous phase with use of a catalyst.

BACKGROUND ART

Patent Literature 1 discloses a method of causing a source material gas, which contains hydrogen and carbon monoxide or carbon dioxide as main components, to react in the presence of a catalyst to synthesize methanol. In the method, methanol liquefied on a cooling surface is taken out of a reaction system so that the reaction of methanol proceeds beyond an equilibrium conversion rate.

In the invention disclosed in Patent Literature 1, in an exothermic reaction such as methanol synthesis, both reaction heat that is generated in a catalyst layer and condensation heat that is generated when a product is liquefied and separated are removed with use of a cooling tube provided on a condensation side.

CITATION LIST

Patent Literature

[Patent Literature 1]
Japanese Patent Application Publication, Tokukai, No. 2005-298413 (Publication Date: Oct. 27, 2005)

SUMMARY OF INVENTION

Technical Problem

However, Patent Literature 1 does not disclose a configuration in which both a temperature environment for reaction and a temperature environment for condensation are achieved in a single reactor in a mode preferable from the perspective of thermal efficiency.

It is an object of an aspect of the present invention to control a temperature environment for reaction and a temperature environment for condensation in a manner preferable from the perspective of thermal efficiency, when causing a chemical reaction for obtaining a product from a source material gas to proceed beyond an equilibrium conversion rate.

Solution to Problem

In order to attain the object, a chemical reaction method in accordance with an aspect of the present invention is a chemical reaction method which causes a reaction to proceed, a product of the reaction containing a component having a boiling point higher than that of a source material gas, progress of the reaction in a gaseous phase being restricted by a chemical equilibrium between a source material and the product, said chemical reaction method using a chemical reaction device including: a catalyst which promotes the reaction; a transmission wall which allows a reacted gas produced by the reaction to pass therethrough; a first heat exchange section positioned on an opposite side from the transmission wall with respect to the catalyst interposed between the first heat exchange section and the transmission wall; and a second heat exchange section spaced apart via a space from the transmission wall, said chemical reaction method including: supplying the source material gas to the catalyst; causing a first heating medium to flow through the first heat exchange section so that a temperature of a surface of the first heat exchange section which surface is in contact with the catalyst is maintained higher than a dew point of the reacted gas; causing a second heating medium to flow through the second heat exchange section so that a temperature of a surface of the second heat exchange section on a space side is maintained not higher than the dew point of the reacted gas; and allowing a liquid obtained by condensation in the space to fall down so as to be separated from the source material gas.

In order to attain the object, a chemical reaction device in accordance with an aspect of the present invention is a chemical reaction device which causes a reaction to proceed, a product of the reaction containing a component having a boiling point higher than that of a source material gas, progress of the reaction in a gaseous phase being restricted by a chemical equilibrium between a source material and the product, the chemical reaction device including: a catalyst to which the source material gas is supplied and which promotes the reaction; a transmission wall which allows a reacted gas produced by the reaction to pass therethrough; a first heat exchange section positioned on an opposite side from the transmission wall with respect to the catalyst interposed between the first heat exchange section and the transmission wall; and a second heat exchange section spaced apart via a space from the transmission wall, a first heating medium being caused to flow through the first heat exchange section so that a temperature of a surface of the first heat exchange section which surface is in contact with the catalyst is maintained higher than a dew point of the reacted gas; a second heating medium being caused to flow through the second heat exchange section so that a temperature of a surface of the second heat exchange section on a side of the space is maintained not higher than the dew point of the reacted gas; and a liquid obtained by condensation in the space is allowed to fall down so as to be separated from the source material gas.

A chemical reaction device in accordance with an aspect of the present invention is a chemical reaction device, including a reaction container including at least one reaction tube that has a multiple structure and that causes a reaction to proceed inside the at least one reaction tube, a product of the reaction containing a component having a boiling point higher than that of a source material gas, progress of the reaction in a gaseous phase being restricted by a chemical equilibrium between a source material and the product, each of the at least one reaction tube including: an inner cylinder which allows a reacted gas produced by the reaction to pass therethrough; an outer cylinder which is included in a first heat exchange section and inside which the inner cylinder is provided; and a second heat exchange section which is provided inside the inner cylinder, the source material gas being supplied to a catalyst layer provided between the inner cylinder and the outer cylinder, a second heating medium being caused to flow through the second heat exchange section so that a temperature of an outer surface of the second heat exchange section is maintained not higher than a dew point of the reacted gas, a liquid obtained by condensation in a first space formed between the second heat exchange section and the inner cylinder being allowed to fall down so as to be separated from the source material gas, a first heating medium being caused to flow on an outer side of the outer cylinder so that a temperature of an inner surface of the outer cylinder is maintained higher than the dew point of the reacted gas.

A chemical reaction device in accordance with an aspect of the present invention is a chemical reaction device, including a reaction container including at least one reaction tube that has a multiple structure and that causes a reaction to proceed inside the at least one reaction tube, a product of the reaction containing a component having a boiling point higher than that of a source material gas, progress of the reaction in a gaseous phase being restricted by a chemical equilibrium between a source material and the product, each of the at least one reaction tube including: an inner cylinder which allows a reacted gas produced by the reaction to pass therethrough; a first heat exchange section which is provided inside the inner cylinder; and an outer cylinder which is included in a second heat exchange section and inside which the inner cylinder is provided, the source material gas being supplied to a catalyst layer provided between the inner cylinder and the first heat exchange section, a second heating medium being caused to flow on an outer side of the outer cylinder so that a temperature of an inner surface of the outer cylinder is maintained not higher than a dew point of the reacted gas, a liquid obtained by condensation in a first space formed between the inner cylinder and the outer cylinder being allowed to fall down so as to be separated from the source material gas, a first heating medium being caused to flow through the first heat exchange section so that a temperature of a surface of the first heat exchange section is maintained higher than the dew point of the reacted gas.

Advantageous Effects of Invention

According to an aspect of the present invention, it is possible to control a temperature environment for reaction and a temperature environment for condensation in a manner preferable from the perspective of thermal efficiency, when causing a chemical reaction for obtaining a product from a source material gas to proceed beyond an equilibrium conversion rate.

DESCRIPTION OF EMBODIMENTS

Embodiment 1

(Configuration of Reaction Device 100)

Figure 1:
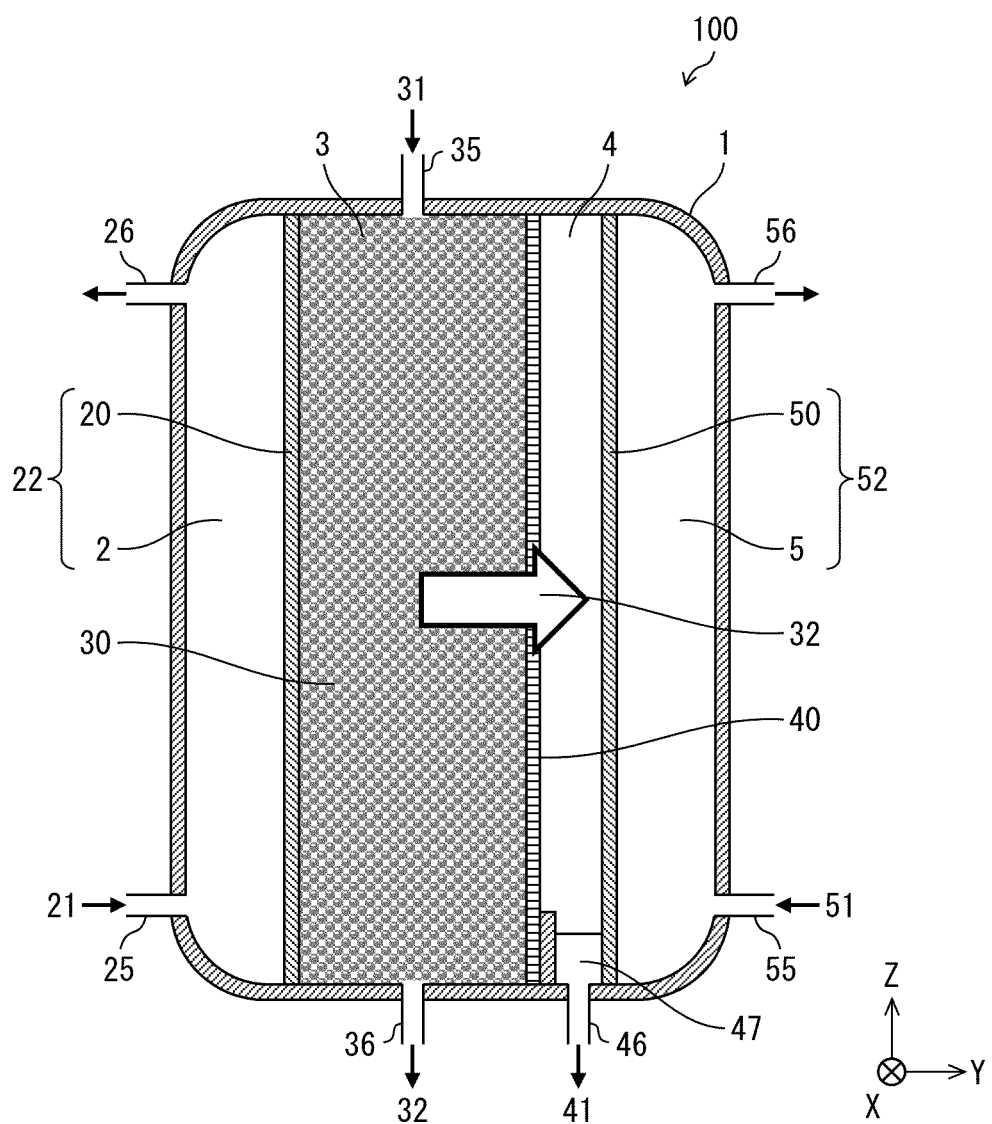
FIG. 1 is a cross-sectional view of a reaction device in accordance with Embodiment 1.

The following description will discuss an embodiment of the present invention in detail. FIG. 1 is a cross-sectional view of a reaction device 100 in accordance with Embodiment 1, the cross-sectional view being taken along a plane perpendicular to a bottom surface of the reaction device 100. The reaction device 100 is a chemical reaction device for carrying out a reaction, a product of which contains a component having a boiling point higher than that of a main component of a source material gas 31 and in which progress of the reaction in a gaseous phase is restricted by a chemical equilibrium between a source material and the product.

In the reaction device 100, the product is obtained by condensation and collected out of a reaction container. This causes the chemical equilibrium to be shifted toward the product and thus enables the reaction to proceed. In particular, the reaction device 100 can be suitably used as a device for carrying out chemical reactions represented by the following formulae (1) through (3), in each of which the source material gas 31 contains a carbon oxide and hydrogen and the product contains methanol.

$$CO + 2H_2 \rightleftharpoons CH_3OH \qquad (1)$$

$$CO_2 + 3H_2 \rightleftharpoons CH_3OC + H_2O \qquad (2)$$

$$CO_2 + H_2 \rightleftharpoons CO + H_2O \qquad (3)$$

Further, the reaction device 100 can be used also for carrying out a reaction that yields dimethyl ether or ammonia as a product.

As illustrated in FIG. 1, the reaction device 100 includes a reaction container 1, a first heat exchange section 22, a catalyst layer 3 in contact with the first heat exchange section 22, a transmission wall 40, and a second heat exchange section 52 spaced apart via a space 4 from the transmission wall 40. The transmission wall 40 is provided on the catalyst layer 3 on a side opposite the first heat exchange section 22. The reaction container 1 is a metal container made of, for example, a stainless steel having pressure resistance.

The first heat exchange section 22 is a heat exchanger constituted by an inner wall surface of the reaction container 1 and a first heat exchange wall 20. Inside the first heat exchange section 22, there is formed a first heating medium region 2, through which a first heating medium 21 is caused to flow. The first heat exchange section 22 has (i) a first heating medium feed opening 25 for supplying the first heating medium 21 to the first heating medium region 2 and (ii) a first heating medium collection opening 26 for discharging the first heating medium 21 from the first heating medium region 2. The first heat exchange wall 20 is made of a member that does not allow fluids to pass therethrough. A surface of the first heat exchange wall 20 on a catalyst layer 3 side serves as a first heat exchange surface. In FIG. 1, the first heat exchange wall 20 is illustrated as a plate-like member. However, a shape of the first heat exchange wall 20 is not limited to a plate-like shape. A surface of the first heat exchange wall 20 can be formed into a wavy shape or the like. Further, a shape of the first heat exchange section 22 is not limited to the shape illustrated in FIG. 1, and can be various shapes that increase an efficiency of heat exchange, such as a multipipe configuration or a spiral shape.

The first heat exchange section 22 can maintain a temperature of the first heat exchange wall 20 higher than a dew point of a reacted gas 32 by letting the first heating medium 21 to flow through the first heating medium region 2. In a case where a reaction that occurs in the catalyst layer 3 is an exothermic reaction, the first heating medium 21 serves as a heating medium for cooling reaction heat generated by the reaction. In a case where a reaction that occurs in the catalyst layer 3 is an endothermic reaction, the first heating medium 21 serves as a heating medium for heating the catalyst layer 3. Thus, the first heating medium maintains a temperature of the catalyst layer 3 not less than the dew point of the reacted gas 32.

Note that the wording "dew point of the reacted gas 32" means a temperature at which condensation starts in a case where the reacted gas 32 is cooled in a state where a reaction in a gaseous phase has reached a chemical equilibrium at a temperature and a pressure at which the reacted gas 32 is present in the catalyst layer 3.

When a composition of the gaseous phase and the pressure are given, the dew point of the reacted gas 32 can be calculated simultaneously as a composition of a condensate by carrying out an appropriate vapor-liquid equilibrium calculation with use of a vapor-liquid equilibrium model. In a case where the pressure is a high pressure exceeding 1 MPa, the vapor-liquid equilibrium model can be, for example, an extended cubic equation of state such as the Peng-Robinson equation or the Redich-Kwong-Soave equation.

The first heat exchange wall 20 more preferably has a temperature that enables a temperature of the entire catalyst layer 3 to be maintained higher than the dew point of the reacted gas 32. Examples of the first heating medium 21 in a case where the product is methanol include high-pressure boiler water (e.g. saturated water at 2.2 MPaG to 5.0 MPaG) at 220° C. to 265° C., a molten metal salt (e.g. a mixture of sodium nitrite and potassium nitrate), and heat transfer oil. Note that numerical expressions such as "A to B" herein mean "not less than A and not more than B".

The second heat exchange section 52 is a heat exchanger constituted by an inner wall surface of the reaction container 1 and a second heat exchange wall 50. Inside the second heat exchange section 52, there is formed a second heating medium region 5, through which a second heating medium 51 is caused to flow. The second heat exchange section 52 has (i) a second heating medium feed opening 55 for supplying the second heating medium 51 to the second heating medium region 5 and (ii) a second heating medium collection opening 56 for discharging the second heating medium 51 from the second heating medium region 5. The second heat exchange wall 50 is made of a member that does not allow fluids to pass therethrough. A surface of the second heat exchange wall 50 on a space 4 side serves as a second heat exchange surface. In FIG. 1, the second heat exchange wall 50 is illustrated as a plate-like member. However, a shape of the second heat exchange wall 50 is not limited to a plate-like shape. A surface of the second heat exchange wall 50 can be formed into a wavy shape or the like. Further, a shape of the second heat exchange section 52 is not limited to the shape illustrated in FIG. 1, and can be various shapes that increase an efficiency of heat exchange, such as a multipipe configuration or a spiral and shape.

The second heat exchange section 52 can maintain a temperature of the second heat exchange wall 50 not higher than the dew point of the reacted gas 32 by letting the second heating medium 51 to flow through the second heating medium region 5. Examples of the second heating medium 51 in a case where the product is methanol include low-pressure boiler water (e.g. saturated water at −0.05 MPaG to 0.4 MPaG) at 80° C. to 150° C., industrial water, ammonia water, a hydrocarbon compound such as pentane, and a chlorofluorocarbon compound such as 1,1,1,3,3-pentafluoropropane.

More specifically, it is preferable that the first heating medium 21 have a temperature lower than an average temperature of the catalyst layer 3 by 5° C. to 30° C. and the second heating medium 51 have a temperature lower than the dew point of the reacted gas 32 by not less than 20° C., in a case where a reaction catalyzed by a catalyst 30 is a exothermic reaction carried out at a temperature higher than the dew point of the reacted gas 32 by not less than 80° C.

Note that the temperature of the first heating medium and the temperature of the second heating medium each mean an average of a temperature at a corresponding feed opening and a temperature at a corresponding collection opening. In the present invention, a greater difference between the temperature of the first heating medium 21 and the temperature of the second heating medium 51 makes it easier to achieve an effect. In the above temperature ranges, the difference between the temperatures of the first heating medium 21 and the second heating medium 51 is at least greater than 70° C. That is, an exergy of heat collected by the first heating medium 21, which is on a reaction side, is significantly greater than an exergy of heat collected by the second heating medium 51, which is on a condensation side. By controlling the temperatures of the first heating medium 21 and the second heating medium 51 within the above temperature ranges and collecting heat, it is possible to effectively utilize reaction heat having a higher exergy.

Note that, in FIG. 1, the first heating medium feed opening 25 and the first heating medium collection opening are formed in a lower part and an upper part, respectively, of the reaction container 1, and the second heating medium feed opening 55 and the second heating medium collection opening 56 are formed in the lower part and the upper part, respectively, of the reaction container 1. It should be understood, however, that these can be formed in appropriate positions in appropriate manners in accordance with pressures of the heating mediums used. Further, a temperature and a pressure at which each of the first heating medium 21 and the second heating medium 51 is supplied can be set to an appropriate value in accordance with a temperature of the reaction carried out in the reaction container 1 and the dew point of the reacted gas 32.

The catalyst layer 3 is filled with the catalyst 30 which is appropriate for the reaction. The catalyst layer 3 is a region in which the source material gas 31 and the catalyst 30 come into contact with each other and the reaction proceeds. Examples of the catalyst 30 can be a catalyst containing copper and zinc oxide as main components.

The transmission wall 40 is made of a porous member that allows gas to pass therethrough. The transmission wall 40 is made of a member that allows the reacted gas 32 to pass therethrough but does not allow the catalyst 30 to pass therethrough. Examples of such a member include a metal mesh having an appropriate pore size. The reacted gas 32 contains an unreacted source material gas and an uncondensed reaction product gas.

The space 4 is formed between the transmission wall 40 and the second heat exchange wall 50. In a lower part of the space 4, there is formed a condensate storing section 47 in which a product (condensate 41) liquefied by condensation on the surface of the second heat exchange wall 50 on the space 4 side can be stored. The condensate 41 is collected through a condensate collection opening 46 formed in a bottom part of the condensate storing section 47. In the present embodiment, a distance between a surface of the transmission wall 40 on the space 4 side and the surface of the second heat exchange wall 50 on the space 4 side is defined as a thickness of the space 4. Further, a distance between the surface of the first heat exchange wall 20 on the catalyst layer 3 side and a surface of the transmission wall 40 on the catalyst layer 3 side is defined as a thickness of the catalyst layer 3. The thickness of the space 4 is preferably 0.01 to 2.0 times, more preferably 0.05 to 1.0 times the thickness of the catalyst layer 3. The space 4 has the above thickness preferably over not less than 80%, more preferably not less than 95% of an entire region of the second heat exchange wall 50 in a vertical direction. In a case where the thickness of the space 4 is less than 0.01 times the thickness of the catalyst layer 3, a heat transfer prevention effect is weak, so that condensation of a product may occur in the catalyst layer 3. In a case where the thickness of the space 4 is more than 2.0 times the thickness of the catalyst layer 3, mass transfer of a product from the catalyst layer 3 to the second heat exchange wall 50 is prevented, so that it is difficult to shift the chemical equilibrium toward the product by condensation.

(Flow of Reaction)

The source material gas 31 is supplied through a source material gas inlet 35 formed at an upper part of the catalyst layer 3, and comes into contact with the catalyst 30 filling the catalyst layer 3, so that a reaction proceeds. The reacted gas 32 produced by the reaction passes through the transmission wall 40 into the space 4. Then, the reacted gas 32 is cooled on the second heat exchange wall 50 down to a temperature not higher than the dew point of the reacted gas 32, so that a product is condensed. The product liquefied by condensation falls down to the condensate storing section 47 and collected through the condensate collection opening 46 as the condensate 41.

The reacted gas 32 passing through the transmission wall 40 from the catalyst layer 3 side contains the unreacted source material gas. However, a main component contained in the unreacted material gas is not condensed on the second heat exchange wall 50. Further, since the condensate storing section 47 is provided in the lower part of the space 4, the unreacted source material gas returns to the catalyst layer 3 instead of being discharged through the condensate collection opening 46 together with the condensate 41.

It is preferable that a flow rate of gas passing through the transmission wall 40 be kept in an appropriate range, so that a ratio of the unreacted source material gas that passes through the space 4 and heads toward an exit of the catalyst layer 3 is not excessively high. In order for the flow rate of the gas to be kept in the appropriate range, for example, a pore ratio of the porous member constituting the transmission wall 40 can be adjusted. Alternatively, in order for the flow rate of the gas to be kept in the appropriate range, a member that serves as a resistance against the flow of the gas can be inserted in the space 4.

The reacted gas 32 containing the source material which has not been reacted in the catalyst layer 3 is collected through the reacted gas collection opening 36.

(Collection of Reaction Heat and Condensation Heat)

The first heating medium 21 is supplied through the first heating medium feed opening 25 as, for example, boiler water at 2.2 MPaG to 5.0 MPaG. In a case where the reaction is an exothermic reaction, the reaction heat generated in the catalyst layer 3 is heat exchanged through the first heat exchange wall 20 and collected by the first heating medium 21. The first heating medium 21 passes through the first heating medium collection opening 26 and is collected into a high-pressure steam separator drum (not illustrated). Then, high pressure steam obtained by gas-liquid separation is utilized, for example, as a power source for compressing the source material.

The second heating medium 51 is supplied through the second heating medium feed opening 55 as, for example, boiler water at 0.05 MPaG. The second heating medium 51 collects heat of the reacted gas 32 by heat exchange through the second heat exchange wall 50. The second heating medium 51 thus reduces a temperature of the reacted gas 32 in the space 4 to not higher than the dew point on the surface of the second heat exchange wall 50. The second heating medium 51 passes through the second heating medium collection opening 56 and is collected into a low-pressure steam separator drum (not illustrated). Then, low pressure steam obtained by gas-liquid separation is utilized, for example, as a heat source in a step of purifying the product.

Effect of Embodiment 1

As described above, the reaction device 100 in accordance with Embodiment 1 is a chemical reaction device that causes a reaction to proceed, wherein a product of the reaction contains a component having a boiling point higher than that of the source material gas 31, and progress of the reaction in a gaseous phase is restricted by a chemical equilibrium between a source material and the product. A chemical reaction method in accordance with Embodiment 1 is a method in which the reaction device 100 is used. The reaction device 100 includes: the catalyst 30 to which the source material gas 31 is supplied and which promotes the reaction; the transmission wall 40 which allows the reacted gas 32 to pass therethrough; the first heat exchange section 22; and the second heat exchange section 52. The first heat exchange section 22 is positioned on an opposite side from the transmission wall 40 with respect to the catalyst 30 interposed between the first heat exchange section 22 and the transmission wall 40, and the second heat exchange section 52 is spaced apart via the space 4 from the transmission wall 40. The second heating medium 51 is caused to flow through the second heat exchange section 52 so that a temperature of the surface of the second heat exchange section 52 on the space 4 side is maintained not higher than the dew point of the reacted gas 32. The liquid (condensate) 41 obtained by condensation in the space 4 falls down so as to be separated from the source material gas 31. The first heating medium 21 is caused to flow through the first heat exchange section 22 so that a temperature of the surface of the first heat exchange section 22 which surface is in contact with the catalyst 30 is maintained higher than the dew point of the reacted gas 32.

According to the reaction device 100 and the chemical reaction method using the reaction device 100, the product is collected out of the reaction container 1 as the condensate 41. This makes it possible to cause a reaction in a reaction system, in which progress of the reaction in a gaseous phase is restricted by a chemical equilibrium, to proceed beyond an equilibrium conversion rate.

Further, the first heat exchange section 22 and the second heat exchange section 52 enable control of both a temperature on a reaction side and a temperature on a condensation side. This enables temperature control in a reaction device to be carried out more easily and reliably. This makes it possible to control a reaction temperature and a condensation temperature in a manner preferable from the perspective of thermal efficiency.

Further, the space 4 in the reaction device 100 provides a distance between the transmission wall 40 and the second heat exchange wall 50. This prevents heat transfer between the catalyst layer 3 and the second heat exchange wall, on which the condensate 41 is produced. This makes it possible to reduce the likelihood that a region of the catalyst layer 3 which region is close to the second heat exchange wall 50 will have a temperature not higher than the dew point of the reacted gas 32. In other words, it is possible to reduce the likelihood that condensation of a product will occur in the catalyst layer 3. Further, the provision of the condensate storing section 47 in the lower part of the space 4 prevents the reacted gas 32 passing through the space 4 from proceeding to flow out of the reaction device. This enables the unreacted source material gas and the catalyst to come into contact with each other more reliably.

Further, it is also an object of the present invention to increase energy use efficiency as compared to conventional levels in a case where the reaction carried out using the reaction device 100 is an exothermic reaction, from the perspective of collecting reaction heat and condensation heat. In a case where the chemical reaction in the reaction device 100 is an exothermic reaction, the reaction device 100 collects reaction heat with use of the first heat exchange section 22 and collects condensation heat with use of the second heat exchange section 52.

By thus separately collecting condensation heat and reaction heat which is higher in temperature than the condensation heat, it is possible to collect heat having a high exergy in comparison to a case where heat is collected only on the condensation side. The collected heat having a high exergy can be utilized in generation of a power source for compressing a source material to be supplied to a high pressure reaction container which is required in a process. Further, the collected heat which has been collected on the condensation side can be efficiently used in a step such as separation and collection of a product. That is, the reaction device 100 increases an energy use efficiency as compared to conventional levels. In view of this, an aspect of the present invention can be considered to be a thermal energy collecting system including the reaction device 100. A reaction device included in the thermal energy collecting system can be a reaction device 100A or a reaction device 100B (described later).

Embodiment 2

The following description will discuss another embodiment of the present invention. For convenience of explanation, the same reference signs will be given to members each having the same function as a member described in Embodiment 1, and descriptions on such a member will be omitted.

Figure 2:
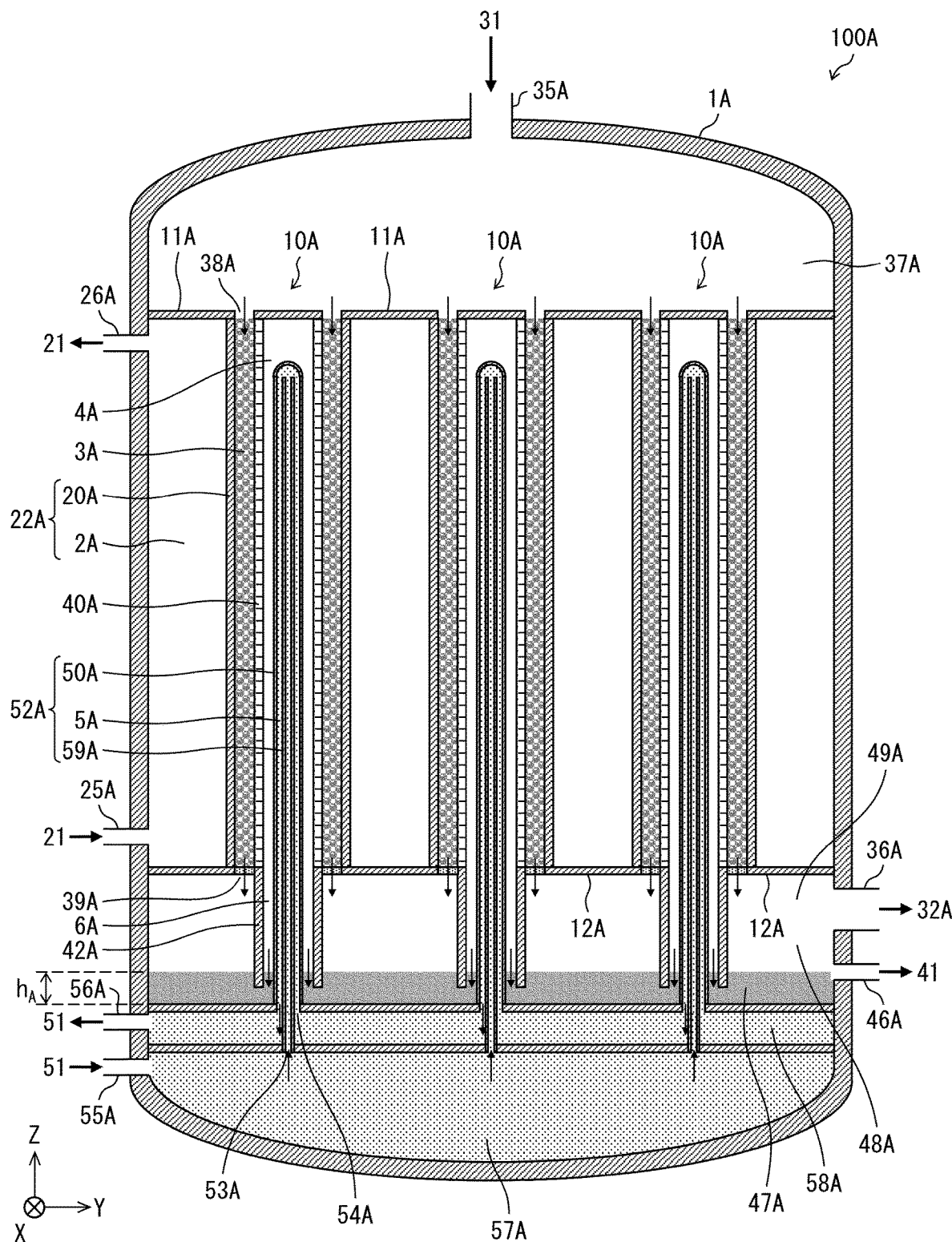
FIG. 2 is a cross-sectional view of a reaction device in accordance with Embodiment 2.
Figure 3:
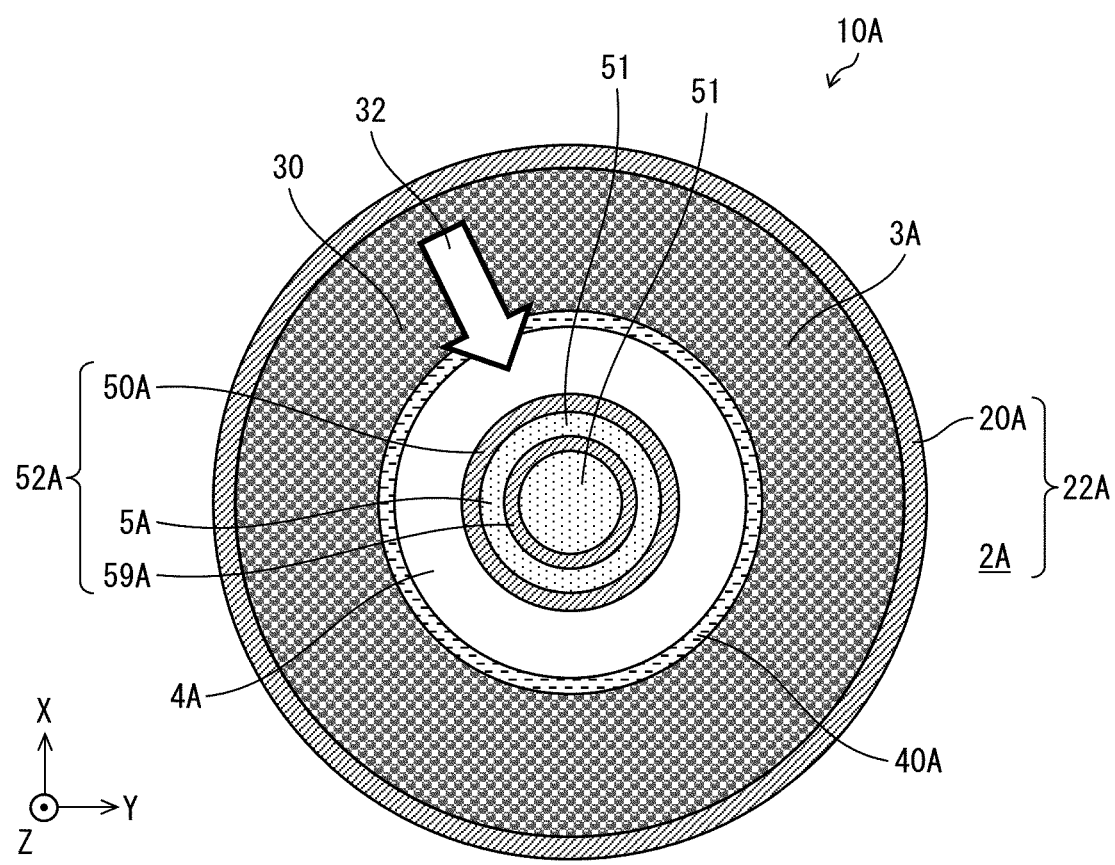
FIG. 3 is a cross-sectional view of a reaction tube included in the reaction device in accordance with Embodiment 2.

FIG. 2 is a cross-sectional view of the reaction device 100A in accordance with Embodiment 2, the cross-sectional view being taken along a plane perpendicular to a bottom surface of the reaction device 100A. FIG. 3 is a cross-sectional view of a reaction tube 10A included in the reaction device 100A, the cross-sectional view being taken along a plane perpendicular to a long axis of the reaction tube 10A. Basic principles of the reaction device 100A are the same as those of the reaction device 100. The reaction device 100A differs from the reaction device 100 in that cylindrical reaction tubes are used in the reaction device 100A.

As with the reaction device 100, the reaction device 100A can be suitably used as a device for carrying out chemical reactions in which a source material gas 31 contains a carbon oxide and hydrogen and the product contains methanol. Further, the reaction device 100A can be used also for carrying out a reaction that yields dimethyl ether or ammonia as a product.

(Reaction Device 100A)

As illustrated in FIG. 2, the reaction device 100A includes a reaction container 1A and a plurality of reaction tubes 10A provided inside the reaction container 1A. The number of the reaction tubes 10A provided inside the reaction container 1A is not particularly limited, provided that the number is at least one. In consideration of reaction efficiency, the number of the reaction tubes 10A is preferably more than one. On an upper side of the plurality of reaction tubes 10A, there is formed a source material gas supplying section 37A which is filled with the source material gas 31 to be supplied to each of the reaction tubes 10A. On a lower side of the plurality of reaction tubes 10A, there is formed a storing section 48A for storing a liquid that has been obtained by condensation inside each reaction tube 10A and gas that has passed through a catalyst layer 3A. On a lower side of the storing section 48A, there is formed a second heating medium collecting section 58A for storing a second heating medium 51 discharged from a second heat exchange section 52A (described later). Further, on a lower side of the second heating medium collecting section 58A, there is formed a second heating medium supplying section 57A for storing the second heating medium 51 to be supplied to the second heat exchange section 52A. The above sections are formed by dividing an inner space of the reaction container 1A with use of metal plates (e.g. stainless steel plates).

The reaction tube 10A is open to a metal plate 11A positioned at an upper part of the reaction tube 10A and to a metal plate 12A positioned at a lower part of the reaction tube 10A. An outer cylinder 20A of the reaction tube 10A is joined to the metal plates 11A and 12A by welding.

As illustrated in FIGS. 2 and 3, the reaction tube 10A includes, in this order from an outer side, the outer cylinder 20A, the catalyst layer 3A which has a cylindrical shape and is in contact with an inner wall surface of the outer cylinder 20A, an inner cylinder 40A provided on an inner side of the catalyst layer 3A, and the second heat exchange section 52A. The second heat exchange section 52A is spaced apart via a space 4A (first space) from the inner cylinder 40A.

A first heat exchange section 22A is a heat exchanger constituted by: a part of an inner wall surface of the reaction container 1A; an outer wall surface of the outer cylinder 20A; and the metal plates 11A and 12A. Inside the first heat exchange section 22A, there is formed a first heating medium region 2A, which is common among the plurality of reaction tubes 10A. In the first heating medium region 2A, a first heating medium 21 is caused to flow. The outer cylinder 20A is made of a member that does not allow fluids to pass therethrough. A surface of the outer cylinder 20A on a catalyst layer 3A side serves as a first heat exchange surface.

A side wall of the reaction container 1A has formed therein (i) a first heating medium feed opening 25A for supplying the first heating medium 21 to the first heating medium region 2A and (ii) a first heating medium collection opening 26A for discharging the first heating medium 21 from the first heating medium region 2A. The first heat exchange section 22A can maintain a temperature of the outer cylinder 20A higher than a dew point of a reacted gas 32 by letting the first heating medium 21 to flow through the first heating medium region 2A.

Figure 4:
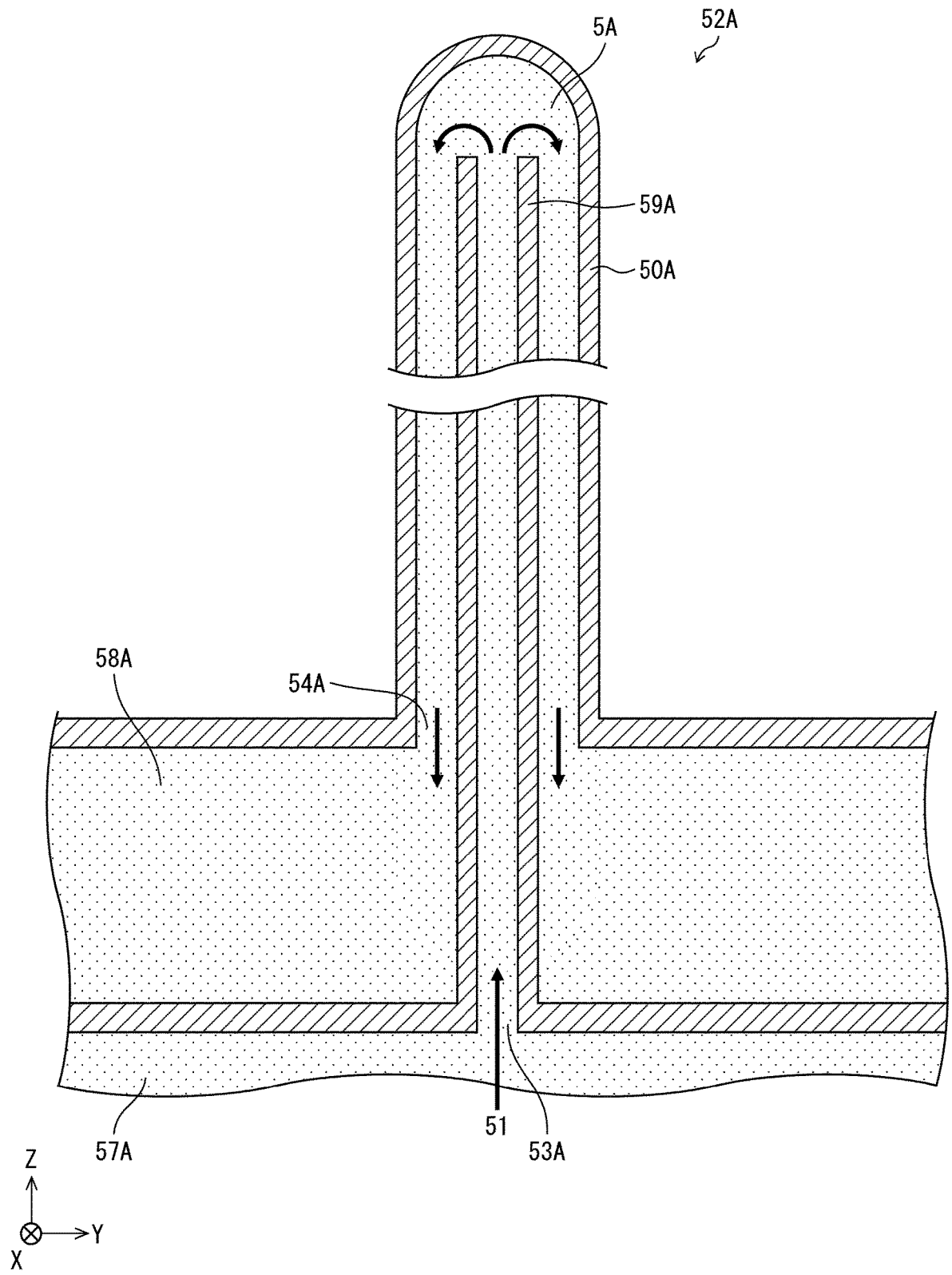
FIG. 4 is a cross-sectional view of a second heat exchange section included in the reaction device in accordance with Embodiment 2.

FIG. 4 is a cross-sectional view of the second heat exchange section 52A, the cross-sectional view being taken along a plane containing a long axis of the second heat exchange section 52A. As illustrated in FIG. 4, the second heat exchange section 52A includes a second heat exchange wall 50A and an inner tube 59A. Between the second heat exchange wall 50A and the inner tube 59A, a second heating medium region 5A is formed. The second heating medium region 5A is a region through which the second heating medium 51 is caused to flow.

The second heat exchange section 52A has a double cylinder structure, and a tip of the inner tube 59A is connected to an inflow port 53A of the second heating medium supplying section 57A. The second heating medium 51 inside the second heating medium supplying section 57A is supplied into the second heat exchange section 52A through the inner tube 59A. A channel between an outer wall surface of the inner tube 59A and an inner wall surface of the second heat exchange wall 50A communicates with an inside of the second heating medium collecting section 58A. The second heating medium 51 that has reached an upper end of the inner tube 59A after exiting the second heating medium supplying section 57A passes through the channel and is discharged to the second heating medium collecting section 58A through an outflow port 54A formed in an upper wall surface of the second heating medium collecting section 58A.

The second heat exchange wall 50A is made of a member that does not allow fluids to pass therethrough. A surface of the second heat exchange wall 50A on a space 4A side serves as a second heat exchange surface. The second heat exchange section 52A can maintain a temperature of the second heat exchange wall 50A not higher than the dew point of the reacted gas 32 by letting the second heating medium 51 to flow through the second heating medium region 5A.

The catalyst layer 3A is filled with the catalyst 30 which is appropriate for the reaction. A portion of an upper end of the reaction tube 10A other than an upper end of the catalyst layer 3A is covered with a metal cap so that it is impossible for gas to flow through the portion. At the upper end of the catalyst layer 3A, there is formed an opening 38A, through which the source material gas 31 is supplied to the catalyst layer 3A. At a lower end of the catalyst layer 3A, an opening 39A is formed. The opening 39A is provided with a supporting member made of, for example, a metal mesh. The supporting member serves to prevent the catalyst 30 from falling down.

The inner cylinder 40A is made of a porous member that allows gas to pass therethrough, and can cause gas that has been produced in the catalyst layer 3A and contains a product and an unreacted source material to pass through the inner cylinder 40A to a second heat exchange section 52A side.

The space 4A is formed between the inner cylinder 40A and the second heat exchange wall 50A. In Embodiment 2, a condensate flow tube (communicating tube) 42A is provided on a vertically lower side of the space 4A. The condensate flow tube 42A is formed so that the space 4A is extended vertically downward. The condensate flow tube 42A is made of a member that does not allow a liquid to pass therethrough. More specifically, the condensate flow tube 42A forms, between itself and a surface of the second heat exchange section 52A, a space (second space) 6A that is continuous with the space 4A. Details of the respective thicknesses of the space 4A and the catalyst layer 3A are similar to those in Embodiment 1. The space 4A has the above thickness preferably over not less than 80%, more preferably not less than 95% of an entire region of the second heat exchange wall 50A in the vertical direction.

On the lower side of the reaction tube 10A, there is formed the storing section 48A which stores therein, on a vertically lower side of the space 4A, the condensate 41 that has been produced in the space 4A and gas that has passed through the catalyst layer 3A. The condensate flow tube 42A is provided inside the storing section 48A, and a lower end of the condensate flow tube 42A is positioned so as to be immersed in the condensate 41 stored in a bottom part (referred to as a "condensate storing section 47A") of the storing section 48A.

In a space (referred to as a "gas collection region 49A") on an upper side inside the storing section 48A, an uncondensed gas 32A that has passed through the catalyst layer 3A is stored. The uncondensed gas 32A is part of the reacted gas 32 which part passes through the catalyst layer 3A without being condensed, flows in the gas collection region 49A (storing section 48A), comes into contact with the condensate storing section (liquid storing section) 47A, and then is discharged. The storing section 48A has an uncondensed gas collection opening 36A (exhaust section) through which the uncondensed gas 32A stored in the gas collection region 49A is discharged. The uncondensed gas collection opening 36A is located vertically above the lower end of the condensate flow tube 42A.

The condensate 41, which is a product obtained by condensation in the space 4A, passes through an inside of the condensate flow tube 42A and is discharged to the condensate storing section 47A. The condensate 41 in the condensate storing section 47A is collected through a condensate collection opening 46A formed in the vicinity of a bottom part of the storing section 48A. At this time, discharge of fluid through the condensate collection opening 46A is controlled to prevent the reacted gas 32 from being collected through the condensate collection opening 46A.

(Flow of Reaction)

The source material gas 31 is supplied through a source material gas inlet 35A, and is supplied to the catalyst layer 3A in the reaction tube 10A through the opening 38A. The source material gas 31 comes into contact with the catalyst 30 in the catalyst layer 3A, so that a reaction proceeds. The reacted gas 32 produced by the reaction passes through the inner cylinder 40A into the space 4A, and is cooled on an outer wall surface (second heat exchange surface) of the second heat exchange wall 50A down to a temperature not higher than the dew point of the reacted gas 32, so that a product is condensed. The product liquefied by condensation falls through the space 4A and the condensate flow tube 42A down to the condensate storing section 47A. The condensate 41 stored in the condensate storing section 47A is collected through the condensate collection opening 46A.

The reacted gas 32 passing through the inner cylinder 40A from the catalyst layer 3A side contains an unreacted source material gas. However, a main component contained in the unreacted source material gas is not condensed on the second heat exchange wall 50A. Further, since the lower end of the condensate flow tube 42A is immersed in the condensate 41 stored in the condensate storing section 47A, the unreacted source material gas traveling inside the condensate flow tube 42A is prevented by a liquid surface of the condensate 41 from moving forward, and returns to the catalyst layer 3A. The gas collection region 49A is under a predetermined pressure due to injection of the source material gas 31, and the liquid surface of the condensate 41 in the condensate storing section 47A is also under the above pressure. As such, the liquid surface prevents the unreacted source material gas from being discharged from the lower end of the condensate flow tube 42A instead of returning to the catalyst layer 3A. Note that a liquid level hA in the condensate storing section 47A is preferably maintained within a range that satisfies the following relationship.

$hA = \alpha \Delta P / \rho g$ $1.0 < \alpha < 10$ hA: the liquid level in the storing section [m]

$\Delta P$: a pressure loss of the reacted gas passing through the catalyst layer [Pa]

$\rho$: a density of the condensate [kg/m$^3$]

g: gravitational acceleration (=9.8 [m/s$^2$])

$\alpha$: coefficient [–]

In a case where hA is too low, part of the reacted gas may pass through the space 4A and the condensate storing section 47A and flow out through the condensate collection opening 46A together with the condensate. This may reduce an efficiency of contact between the reacted gas and the catalyst 30. In a case where hA is too high, a height of the reaction container may be increased, and a pressure in the space 4A may become higher than that in the catalyst layer 3A. This may prevent transfer of the product from the catalyst layer 3A to the space 4A.

The uncondensed gas 32A containing a source material that has not been reacted in the catalyst layer 3A is collected into the gas collection region 49A and collected through the uncondensed gas collection opening 36A formed in an upper part of the storing section 48A.

(Collection of Reaction Heat and Condensation Heat)

The first heating medium 21 is supplied to the first heat exchange section 22A through the first heating medium feed opening 25A. Reaction heat generated in the catalyst layer 3A is heat exchanged through the outer cylinder 20A and collected by the first heating medium 21. The first heating medium 21 passes through the first heating medium collection opening 26A and is collected into a high-pressure steam separator drum (not illustrated). Then, high pressure steam obtained by gas-liquid separation is utilized, for example, as a power source for compressing the source material.

The second heating medium 51 is supplied to the second heating medium supplying section 57A through a second heating medium feed opening 55A, and then is supplied to the second heat exchange section 52A. The second heating medium 51 collects heat of the reacted gas 32 by heat exchange through the second heat exchange wall 50A. This causes a temperature of the reacted gas 32 in the space 4A to be reduced not higher than the dew point on the surface of the second heat exchange wall 50A. The second heating medium 51 passes through the second heating medium collection opening 56A and is collected into a low-pressure steam separator drum (not illustrated). Then, low pressure steam obtained by gas-liquid separation is utilized, for example, as a heat source in a step of purifying the product.

Effect of Embodiment 2

As described above, the reaction device 100A includes the reaction container 1A including at least one reaction tube 10A that has a multiple structure and that causes a reaction to proceed inside the at least one reaction tube 10A, wherein a product of the reaction contains a component having a boiling point higher than that of the source material gas 31, and progress of the reaction in a gaseous phase is restricted by a chemical equilibrium between a source material and the product. Each reaction tube 10A includes: the inner cylinder 40A which allows the reacted gas 32 produced by the reaction to pass therethrough; the outer cylinder 20A which is included in the first heat exchange section 22A and inside which the inner cylinder 40A is provided; and the second heat exchange section 52A which is provided inside the inner cylinder 40A. The source material gas 31 is supplied to the catalyst layer 3A provided between the inner cylinder 40A and the outer cylinder 20A. The second heating medium 51 is caused to flow through the second heat exchange section 52A so that a temperature of an outer surface of the second heat exchange section 52A is maintained not higher than the dew point of the reacted gas 32. The liquid obtained by condensation in the space 4A (first space) formed between the second heat exchange section 52A and the inner cylinder 40A falls down so as to be separated from the source material gas. Further, the first heating medium 21 is caused to flow on an outer side of the outer cylinder 20A so that a temperature of an inner surface of the outer cylinder 20A is maintained higher than the dew point of the reacted gas 32.

According to the reaction device 100A and a chemical reaction method using the reaction device 100 configured as described above, the product is collected out of the reaction device 100A as the condensate 41. This makes it possible to cause a reaction in a reaction system, in which progress of the reaction in a gaseous phase is restricted by a chemical equilibrium, to proceed beyond an equilibrium conversion rate.

Further, the first heat exchange section 22A and the second heat exchange section 52A enable control of both a temperature on a reaction side and a temperature on a condensation side. This enables temperature control in a reaction device to be carried out more easily and reliably. This makes it possible to control a reaction temperature and a condensation temperature in a manner preferable from the perspective of thermal efficiency.

Further, with the reaction device 100A, reaction heat and condensation heat can be collected separately. This makes it possible to collect heat having a high exergy in comparison to a case where heat is collected only on the condensation side. The collected heat having a high exergy can be utilized in generation of a power source for compressing a source material to be supplied to a high pressure reaction container which is required in a process. Further, the collected heat which has been collected on the condensation side can be efficiently used in a step such as separation and collection of a product. That is, the energy use efficiency is significantly increased.

Further, according to the reaction device 100A, the space 4A provides a distance between the inner cylinder 40A and the second heat exchange wall 50A. This prevents heat transfer between the catalyst layer 3A and the second heat exchange wall 50A, on which the condensate 41 is produced. This makes it possible to reduce the likelihood that a region of the catalyst layer 3A which region is close to the second heat exchange wall 50A will have a temperature not higher than the dew point of the reacted gas 32. In other words, it is possible to reduce the likelihood that condensation of a product will occur in the catalyst layer 3A.

Further, with the reaction device 100A, the provision of the condensate storing section 47A in lower parts of the space 4A and the condensate flow tube 42A prevents the reacted gas 32 passing through the space 4 from proceeding to flow out of the reaction device 100A. This enables the reacted gas 32 and the catalyst 30 to come into contact with each other more reliably.

Embodiment 3

The following description will discuss another embodiment of the present invention. In Embodiment 2, as indicated by FIG. 2, the first heating medium 21 for collecting reaction heat can be used in a greater amount in comparison to the second heating medium 51 for collecting condensation heat. That is, the reaction device 100A in Embodiment 2 has a configuration that is advantageous in a reaction system in which removal of reaction heat is important.

In contrast, the reaction device 100B in Embodiment 3, which will be described below in detail, has a configuration that is advantageous in a reaction system in which removal of condensation heat is important. Basic principles of the reaction device 100B are the same as those of the reaction device 100A.

As with the reaction device 100, the reaction device 100B can be suitably used as a device for carrying out chemical reactions in which a source material gas 31 contains a carbon oxide and hydrogen and a product contains methanol. Further, the reaction device 100B can be used also for carrying out a reaction that yields dimethyl ether or ammonia as a product.

Figure 5:
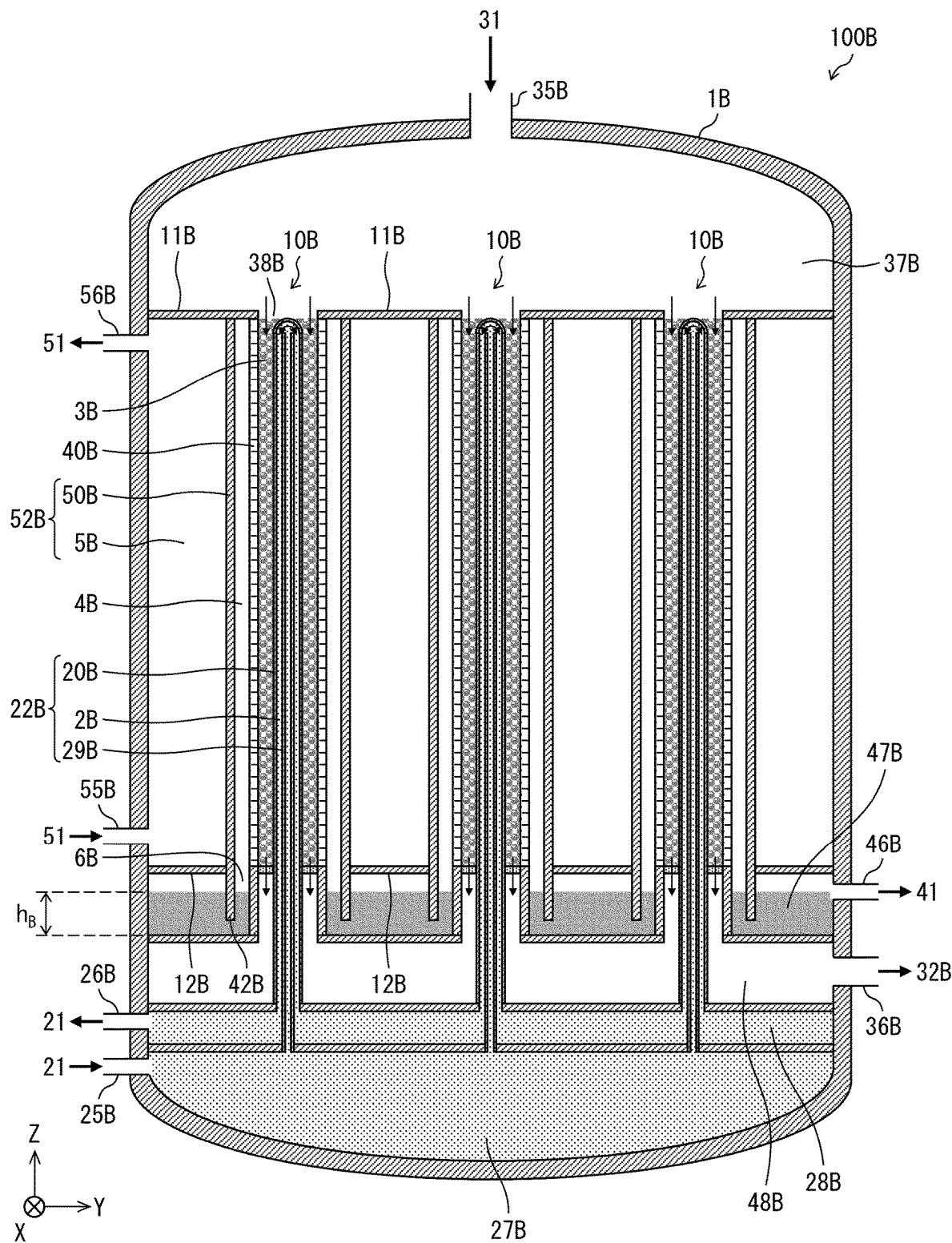
FIG. 5 is a cross-sectional view of a reaction device in accordance with Embodiment 3.
Figure 6:
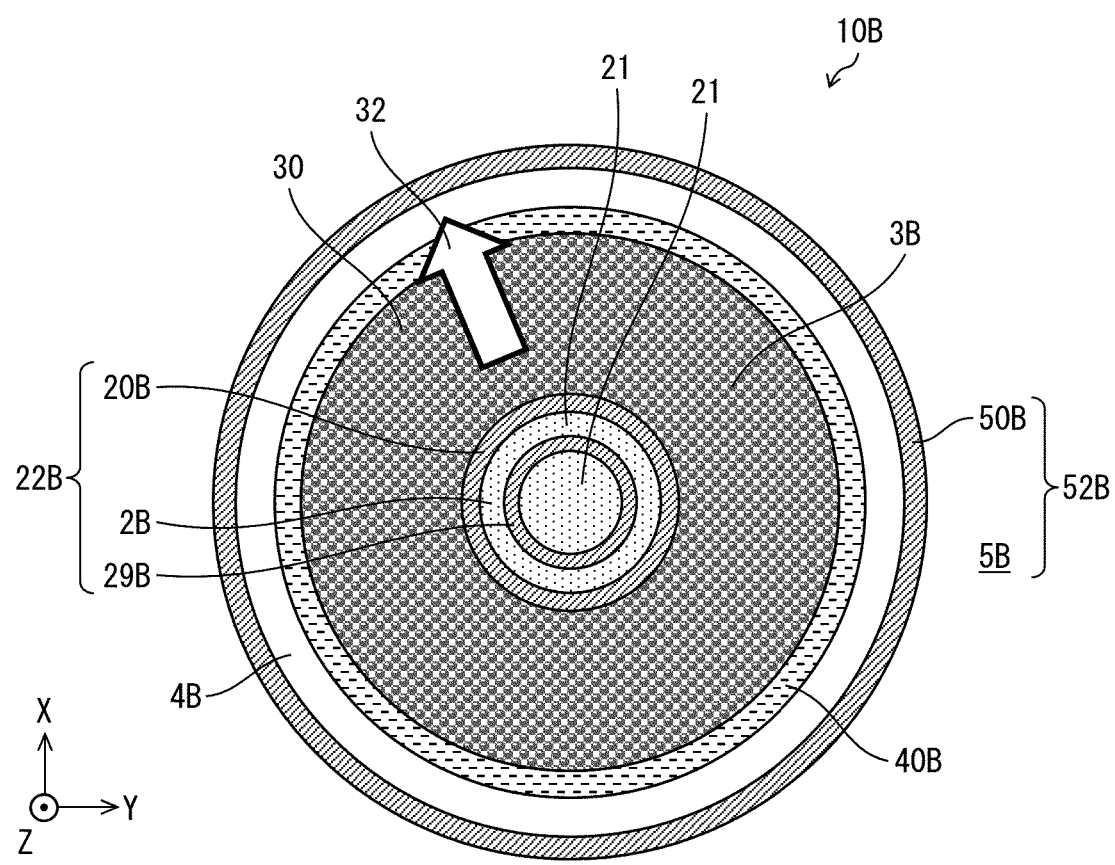
FIG. 6 is a cross-sectional view of a reaction tube included in the reaction device in accordance with Embodiment 3.

FIG. 5 is a cross-sectional view of the reaction device 100B, the cross-sectional view being taken along a plane perpendicular to a bottom surface of the reaction device 100B. FIG. 6 is a cross-sectional view of a reaction tube 10B included in the reaction device 100B, the cross-sectional view being taken along a plane perpendicular to a long axis of the reaction tube 10B.

(Reaction Device 100B)

As illustrated in FIGS. 5 and 6, the reaction device 100B includes a reaction container 1B and a plurality of reaction tubes 10B provided inside the reaction container 1B. The number of the reaction tubes 10B provided inside the reaction container 1B is not particularly limited, provided that the number is at least one. In consideration of reaction efficiency, the number of the reaction tubes 10B is preferably more than one. On an upper side of the plurality of reaction tubes 10B, there is formed a source material gas supplying section 37B which is filled with the source material gas 31 to be supplied to each of the reaction tubes 10B. On a lower side of the plurality of reaction tubes 10B, there is formed a condensate storing section 47B (liquid storing section) for storing a liquid that has been obtained by condensation inside each reaction tube 10B. On a lower side of the condensate storing section 47B, there is formed a gas collecting section 48B which stores therein gas that has passed through a catalyst layer 3B. On a lower side of the gas collecting section 48B, there is formed a first heating medium collecting section 28B which stores therein a first heating medium 21 discharged from a first heat exchange section 22B (described later). Further, on a lower side of the first heating medium collecting section 28B, there is formed a first heating medium supplying section 27B which stores therein the first heating medium 21 to be supplied to the first heat exchange section 22B. The above sections are formed by dividing an inner space of the reaction container 1B with use of metal plates (e.g. stainless steel plates).

The reaction tube 10B includes, in this order from an outer side, an outer cylinder 50B, an inner cylinder 40B spaced apart via a space 4B (first space) from an inner wall surface of the outer cylinder 50B, the catalyst layer 3B which has a cylindrical shape and is in contact with an inner wall surface of the inner cylinder 40B, and the first heat exchange section 22B provided inside the catalyst layer 3B. The catalyst layer 3B is similar to the catalyst layer 3A in material and structure. The inner cylinder 40B is similar to the inner cylinder 40A in material and structure.

A second heat exchange section 52B is a heat exchanger constituted by: a part of an inner wall surface of the reaction container 1B; an outer wall surface of the outer cylinder 50B; and metal plates 11B and 12B. Inside the second heat exchange section 52B, there is formed a second heating medium region 5B, which is common among the plurality of reaction tubes 10B. In the second heating medium region 5B, a second heating medium 51 is caused to flow. The outer cylinder 50B is made of a member that does not allow fluids to pass therethrough. The inner wall surface of the outer cylinder 50B serves as a second heat exchange surface.

On a side wall of the reaction container 1B, there are formed (i) a second heating medium feed opening 55B for supplying the second heating medium 51 to the second heating medium region 5B and (ii) a second heating medium collection opening 56B for discharging the second heating medium 51 from the second heating medium region 5B. The second heat exchange section 52B can maintain a temperature of the outer cylinder 50B not higher than a dew point of a reacted gas 32 by letting the second heating medium 51 to flow through the second heating medium region 5B.

Figure 7:
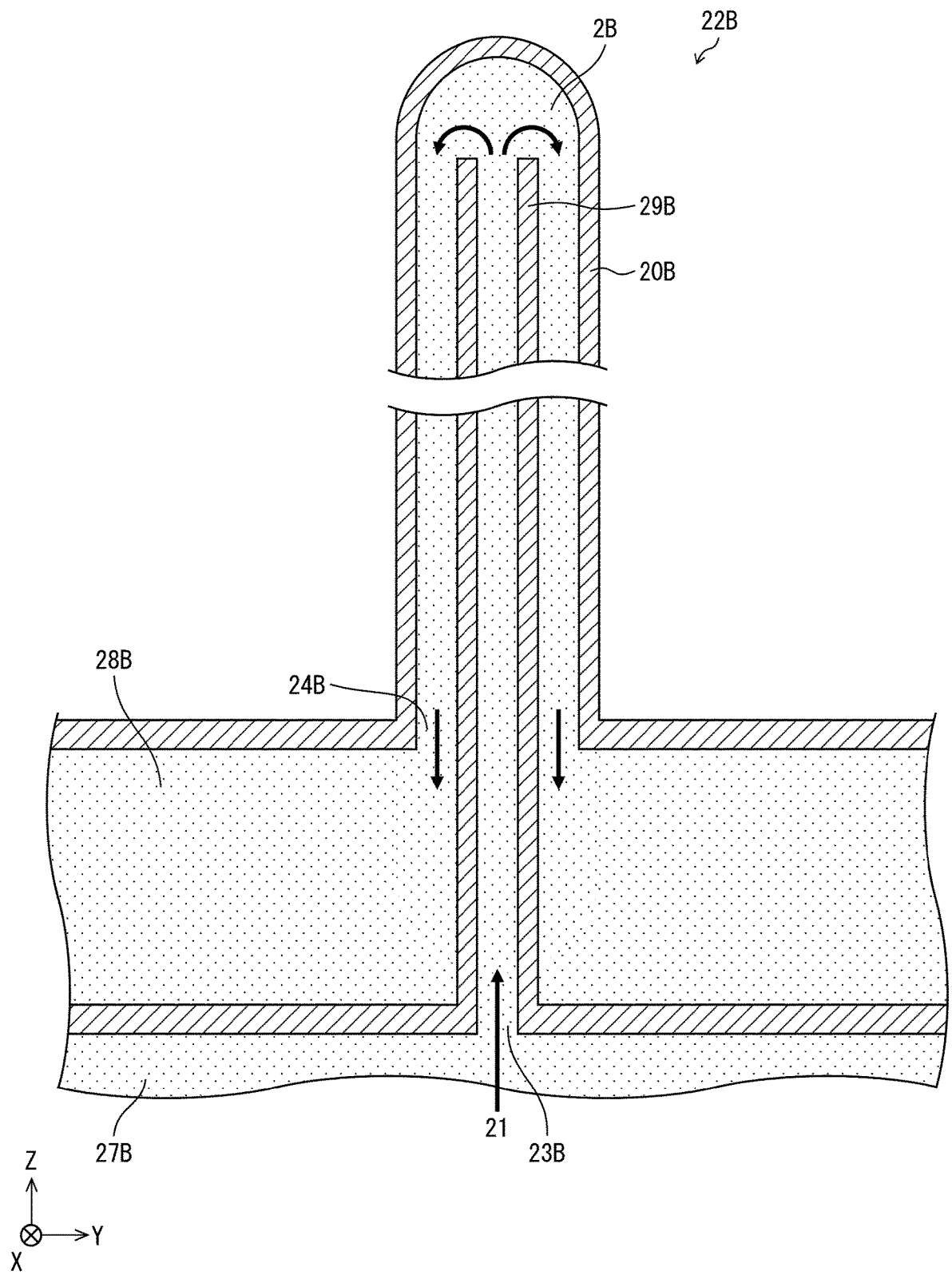
FIG. 7 is a cross-sectional view of a first heat exchange section included in the reaction device in accordance with Embodiment 3.

FIG. 7 is a cross-sectional view of the first heat exchange section 22B, the cross-sectional view being taken along a plane containing a long axis of the first heat exchange section 22B. As illustrated in FIG. 7, the first heat exchange section 22B includes a first heat exchange wall 20B and an inner tube 29B. Between the first heat exchange wall 20B and the inner tube 29B, a first heating medium region 2B is formed. The first heating medium region 2B is a region through which the first heating medium 21 is caused to flow.

The first heat exchange section 22B has a double cylinder structure, and a tip of the inner tube 29B is connected to an inflow port 23B of the first heating medium supplying section 27B. The first heating medium 21 inside the first heating medium supplying section 27B is supplied into the first heat exchange section 22B through the inner tube 29B. A channel between an outer wall surface of the inner tube 29B and an inner wall surface of the first heat exchange wall 20B communicates with an inside of the first heating medium collecting section 28B. The first heating medium 21 that has passed through an inside of the inner tube 29B passes through the channel, and is discharged to the first heating medium collecting section 28B through an outflow port 24B formed in an upper wall surface of the first heating medium collecting section 28B.

The space 4B is formed between the inner cylinder 40B and the outer cylinder 50B. In Embodiment 3, the condensate storing section 47B is provided on a vertically lower side of the space 4B. Further, a condensate flow tube 42B (extension tube) is provided inside the condensate storing section 47B so as to extend the outer cylinder 50B vertically downward. A lower end of the condensate flow tube 42B is positioned so as to be immersed in a condensate 41 stored in the condensate storing section 47B. The condensate flow tube 42B forms, inside the condensate storing section 47B, a space (second space) 6B that is continuous with the space 4B. Details of the respective thicknesses of the space 4B and the catalyst layer 3B are similar to those in Embodiment 1. The space 4B has the above thickness preferably over not less than 80% of an entire region of the outer cylinder 50B in the vertical direction.

A liquid (condensate 41) obtained by condensation in the space 4B passes through the space 6B on an inner side of the condensate flow tube 42B and is stored in the condensate storing section 47B. The condensate 41 stored in the condensate storing section 47B is collected through a condensate collection opening 46B. At this time, discharge of fluid through the condensate collection opening 46B is controlled to prevent the reacted gas 32 from being collected through the condensate collection opening 46B.

On a vertically lower side of the catalyst layer 3B is the gas collecting section 48B (gas storing section) into which gas that has passed through the catalyst layer 3B flows. The gas collecting section 48B has an uncondensed gas collection opening 36B (exhaust section).

Thus, the condensate storing section 47B and the gas collecting section 48B form respective different spaces. The condensate storing section 47B forms a closed space in terms of gas. As such, the source material gas 31 that has descended in the space 4B comes to a dead end and returns to the catalyst layer 3B. This makes it possible to reduce the likelihood that the source material gas 31 passing through the space 4B will proceed to be discharged to an outside.

The first heat exchange section 22B penetrates through the gas collecting section 48B, and a lower end of the inner tube 29B of the first heat exchange section 22B is open to an inner space of the first heating medium supplying section 27B. The channel between the outer wall surface of the inner tube 29B and the inner wall surface of the first heat exchange wall 20B communicates with the inside of the first heating medium collecting section 28B. The first heating medium 21 that has reached an upper end of the inner tube 29B after exiting the first heating medium supplying section 27B passes through the channel and is discharged to the first heating medium collecting section 28B through the outflow port 24B in the upper wall surface of the first heating medium collecting section 28B.

(Flow of Reaction)

The source material gas 31 is supplied through a source material gas inlet 35B, and is supplied to the catalyst layer 3B in the reaction tube 10B through an opening 38B. The source material gas 31 comes into contact with the catalyst 30 in the catalyst layer 3B, so that a reaction proceeds. The reacted gas 32 produced by the reaction passes through the inner cylinder 40B into the space 4B, and is cooled on the inner wall surface (second heat exchange surface) of the outer cylinder 50B down to a temperature not higher than the dew point of the reacted gas 32, so that a product is condensed. The product liquefied by condensation passes through the space 4B and falls down to the condensate storing section 47B. The condensate 41 stored in the condensate storing section 47B is collected through the condensate collection opening 46B.

The reacted gas 32 passing through the inner cylinder 40B from a catalyst layer 3B side toward the outer cylinder 50B contains an unreacted source material gas. However, a main component contained in the unreacted source material gas is not condensed on the outer cylinder 50B. Further, since the condensate storing section 47B forms a closed space in terms of gas, the unreacted source material gas that has descended in the space 4B comes to a dead end and is prevented by a liquid surface of the condensate 41 from moving forward. Thus, the unreacted source material gas returns to the catalyst layer 3B. Note that a liquid level hB in the condensate storing section 47B is preferably maintained within a range that satisfies the following relationship.

$hB = \alpha \Delta P / \rho g$
$1.0 < \alpha < 10$
hB: the liquid level in the storing section [m]
$\Delta P$: a pressure loss of the reacted gas passing through the catalyst layer [Pa]
$\rho$: a density of the condensate [kg/m$^3$]
g: gravitational acceleration (=9.8 [m/s$^2$])
$\alpha$: coefficient [-]

In a case where hB is too low, part of the reacted gas 32 may pass through the space 4B and the condensate storing section 47B and flow out through the condensate collection opening 46B together with the condensate. This may reduce an efficiency of contact between the reacted gas 32 and the catalyst 30. In a case where hB is too high, a height of the reaction container may be increased, and a pressure in the space 4B may become higher than that in the catalyst layer 3B. This may prevent mass transfer of the product from the catalyst layer 3B to the space 4B.

An uncondensed gas 32B containing a source material that has descended in the catalyst layer 3B without being reacted in the catalyst layer 3B is collected into the gas collection region 48B and collected through the uncondensed gas collection opening 36B in the gas collecting section 48B.

(Collection of Reaction Heat and Condensation Heat)

The first heating medium 21 is supplied to the first heating medium supplying section 27B through a first heating medium feed opening 25B, and then is supplied to the first heat exchange section 22B. Reaction heat generated in the catalyst layer 3B is heat exchanged through the first heat exchange wall 20B and collected by the first heating medium 21. The first heating medium 21 passes through a first heating medium collection opening 26B and is collected into a high-pressure steam separator drum (not illustrated). Then, high pressure steam obtained by gas-liquid separation is utilized, for example, as a power source for compressing the source material.

The second heating medium 51 is supplied to the second heat exchange section 52B through the second heating medium feed opening 55B. The second heating medium 51 carries out heat exchange through the outer cylinder 50B to thereby reduce a temperature of the reacted gas 32 in the space 4B to or below the dew point and collect heat of the reacted gas 32. The second heating medium 51 passes through the second heating medium collection opening 56B and is collected into a low-pressure steam separator drum (not illustrated). Then, low pressure steam obtained by gas-liquid separation is utilized, for example, as a heat source in a step of purifying the product.

Effect of Embodiment 3

As described above, the reaction device 100B in accordance with Embodiment 3 includes the reaction container 1B including at least one reaction tube 10B that has a multiple structure and that causes a reaction to proceed inside the at least one reaction tube 10B, wherein a product of the reaction contains a component having a boiling point higher than that of the source material gas 31, and progress of the reaction in a gaseous phase is restricted by a chemical equilibrium between a source material and the product. Each reaction tube 10B includes: the inner cylinder 40B which allows the reacted gas 32 to pass therethrough; the first heat exchange section 22B which is provided inside the inner cylinder 40B; and the outer cylinder 50B which is included in the second heat exchange section 52B and in which the inner cylinder 40B is provided. The source material gas 31 is supplied to the catalyst layer 3B provided between the inner cylinder 40B and the first heat exchange section 22B. The second heating medium 51 is caused to flow on an outer side of the outer cylinder 50B so that a temperature of an inner surface of the outer cylinder 50B is maintained not higher than the dew point of the reacted gas 32. The liquid obtained by condensation in the space (first space) 4B formed between the inner cylinder 40B and the outer cylinder 50B falls down so as to be separated from the source material gas 31. The first heating medium 21 is caused to flow through the first heat exchange section 22B so that a temperature of a surface of the first heat exchange section 22B is maintained higher than the dew point of the reacted gas 32.

According to the reaction device 100B and a chemical reaction method using the reaction device 100B, the product is collected out of the reaction device 100B as the condensate 41. This makes it possible to cause a reaction to proceed beyond an equilibrium conversion rate.

Further, the first heat exchange section 22B and the second heat exchange section 52B enable control of both a temperature on a reaction side and a temperature on a condensation side. This enables temperature control in a reaction device to be carried out more easily and reliably. This makes it possible to control a reaction temperature and a condensation temperature in a manner preferable from the perspective of thermal efficiency.

Further, the space 4B provides a distance between the inner cylinder 40B and the outer cylinder 50B. This prevents heat transfer between the catalyst layer 3B and the outer cylinder 50B, on which the condensate 41 is produced. This makes it possible to reduce the likelihood that a region of the catalyst layer 3B which region is close to the outer cylinder 50B will have a temperature not higher than the dew point of the reacted gas 32. In other words, it is possible to reduce the likelihood that condensation of a product will occur in the catalyst layer 3B and the inner cylinder 40B.

Further, with the reaction device 100B in accordance with Embodiment 3, the provision of the condensate flow tube 42B, the condensate storing section 47B and the gas collecting section 48B prevents the reacted gas 32 passing through the space 4B from proceeding to flow out of the reaction device 100B. This enables the reacted gas 32 and the catalyst 30 to come into contact with each other more reliably.

Further, with the reaction device 100B in accordance with Embodiment 3, reaction heat and condensation heat can be collected separately in a case where the reaction is an exothermic reaction. This makes it possible to collect heat having a high exergy in comparison to a case where heat is collected only on the condensation side. That is, the reaction device 100B increases an energy use efficiency as compared to conventional levels.

REFERENCE SIGNS LIST 1, 1A, 1B: reaction container
2, 2A, 2B: first heating medium region
3, 3A, 3B: catalyst layer
4: space
4A, 4B: first space (space)
5, 5A, 5B: second heating medium region
6A, 6B: space (second space)
10A, 10B: reaction tube
20, 20B: first heat exchange wall
20A: outer cylinder
21: first heating medium
22, 22A, 22B: first heat exchange section
30: catalyst
31: source material gas
32: reacted gas
32A, 32B: uncondensed gas
36: reacted gas collection opening (exhaust section)
36A, 36B: uncondensed gas collection opening (exhaust section)
40: transmission wall
40A, 40B: inner cylinder
42A: condensate flow tube (communicating tube)
42B: condensate flow tube (extension tube)
47A, 47B: condensate storing section (liquid storing section)
48A: storing section
48B: gas collecting section (gas storing section)
50, 50A: second heat exchange wall
50B: outer cylinder
51: second heating medium
52, 52A, 52B: second heat exchange section
100, 100A, 100B: reaction device

The invention claimed is:

1. A chemical reaction method which causes a reaction to proceed, a product of the reaction containing a component having a boiling point higher than that of a source material gas, progress of the reaction in a gaseous phase being restricted by a chemical equilibrium between a source material and the product, said chemical reaction method using a chemical reaction device including:
a catalyst which promotes the reaction;
a transmission wall which allows a reacted gas produced by the reaction to pass therethrough;
a first heat exchange section positioned on an opposite side from the transmission wall with respect to the catalyst interposed between the first heat exchange section and the transmission wall; and
a second heat exchange section spaced apart via a space from the transmission wall, said chemical reaction method comprising:
supplying the source material gas to the catalyst;
causing a first heating medium to flow through the first heat exchange section so that a temperature of a surface of the first heat exchange section which surface is in contact with the catalyst is maintained higher than a dew point of the reacted gas;
causing a second heating medium to flow through the second heat exchange section so that a temperature of a surface of the second heat exchange section on a space side is maintained not higher than the dew point of the reacted gas; and
allowing a liquid obtained by condensation in the space to fall down so as to be separated from the source material gas.

2. The chemical reaction method as set forth in claim 1, wherein:
the reaction catalyzed by the catalyst is an exothermic reaction and carried out at a temperature higher than the dew point of the reacted gas by not less than 80° C.;
the first heating medium has a temperature lower than an average temperature of a catalyst layer containing the catalyst by 5° C. to 30° C.; and
the second heating medium has a temperature lower than the dew point of the reacted gas by not less than 20° C.

3. The chemical reaction method as set forth in claim 1, wherein the source material gas contains a carbon oxide and hydrogen, and the product contains methanol.

4. A chemical reaction device which causes a reaction to proceed, a product of the reaction containing a component having a boiling point higher than that of a source material gas, progress of the reaction in a gaseous phase being restricted by a chemical equilibrium between a source material and the product,
the chemical reaction device comprising:
  a catalyst to which the source material gas is supplied and which promotes the reaction;
  a transmission wall which allows a reacted gas produced by the reaction to pass therethrough;
  a first heat exchange section positioned on an opposite side from the transmission wall with respect to the catalyst interposed between the first heat exchange section and the transmission wall; and
  a second heat exchange section spaced apart via a space from the transmission wall,
  a first heating medium being caused to flow through the first heat exchange section so that a temperature of a surface of the first heat exchange section which surface is in contact with the catalyst is maintained higher than a dew point of the reacted gas;
  a second heating medium being caused to flow through the second heat exchange section so that a temperature of a surface of the second heat exchange section on a side of the space is maintained not higher than the dew point of the reacted gas; and
  a liquid obtained by condensation in the space is allowed to fall down so as to be separated from the source material gas.

5. A chemical reaction device, comprising
a reaction container including at least one reaction tube that has a multiple structure and that causes a reaction to proceed inside the at least one reaction tube, a product of the reaction containing a component having a boiling point higher than that of a source material gas, progress of the reaction in a gaseous phase being restricted by a chemical equilibrium between a source material and the product,
each of the at least one reaction tube including:
  an inner cylinder which allows a reacted gas produced by the reaction to pass therethrough;
  an outer cylinder which is included in a first heat exchange section and inside which the inner cylinder is provided; and
  a second heat exchange section which is provided inside the inner cylinder,
  the source material gas being supplied to a catalyst layer provided between the inner cylinder and the outer cylinder,
  a second heating medium being caused to flow through the second heat exchange section so that a temperature of an outer surface of the second heat exchange section is maintained not higher than a dew point of the reacted gas,
  a liquid obtained by condensation in a first space formed between the second heat exchange section and the inner cylinder being allowed to fall down so as to be separated from the source material gas,
  a first heating medium being caused to flow on an outer side of the outer cylinder so that a temperature of an inner surface of the outer cylinder is maintained higher than the dew point of the reacted gas.

6. The chemical reaction device as set forth in claim 5, further comprising:
  a storing section which stores therein, on a vertically lower side of the first space, the liquid and gas that has passed through the catalyst layer; and
  a communicating tube which is provided inside the storing section,
  the communicating tube forming, between the communicating tube and a surface of the second heat exchange section, a second space continuous with the first space,
  a lower end of the communicating tube being positioned so as to be immersed in the liquid stored in the storing section.

7. The chemical reaction device as set forth in claim 6, wherein:
  the storing section includes an exhaust section through which the gas stored inside the storing section is discharged; and
  the exhaust section is located vertically above the lower end of the communicating tube.

8. A chemical reaction device, comprising
a reaction container including at least one reaction tube that has a multiple structure and that causes a reaction to proceed inside the at least one reaction tube, a product of the reaction containing a component having a boiling point higher than that of a source material gas, progress of the reaction in a gaseous phase being restricted by a chemical equilibrium between a source material and the product,
each of the at least one reaction tube including:
  an inner cylinder which allows a reacted gas produced by the reaction to pass therethrough;
  a first heat exchange section which is provided inside the inner cylinder; and
  an outer cylinder which is included in a second heat exchange section and inside which the inner cylinder is provided,
  the source material gas being supplied to a catalyst layer provided between the inner cylinder and the first heat exchange section,
  a second heating medium being caused to flow on an outer side of the outer cylinder so that a temperature of an inner surface of the outer cylinder is maintained not higher than a dew point of the reacted gas,
  a liquid obtained by condensation in a first space formed between the inner cylinder and the outer cylinder being allowed to fall down so as to be separated from the source material gas,
  a first heating medium being caused to flow through the first heat exchange section so that a temperature of a surface of the first heat exchange section is maintained higher than the dew point of the reacted gas.

9. The chemical reaction device as set forth in claim 8, further comprising:
  a liquid storing section which stores the liquid therein on a vertically lower side of the first space;
  a gas storing section which stores therein, on a vertically lower side of the catalyst layer, gas that has passed through the catalyst layer; and
  an extension tube which is provided inside the liquid storing section,
  the extension tube forming, inside the liquid storing section, a second space continuous with the first space, a lower end of the extension tube being positioned so as to be immersed in the liquid stored in the liquid storing section, the liquid storing section and the gas storing section forming respective different spaces.

* * * * *